US011521401B2

(12) United States Patent
Holland (10) Patent No.: US 11,521,401 B2
(45) Date of Patent: Dec. 6, 2022

(54) FERTILITY WINDOW PREDICTION USING A CONVOLUTIONAL NEURAL NETWORK (CNN) AND OTHER LEARNING METHODS

(71) Applicant: Bridging Biosciences, LLC, Frisco, TX (US)

(72) Inventor: Tapley Holland, Celina, TX (US)

( * ) Notice: Subject to any disclaimer, the term of this patent is extended or adjusted under 35 U.S.C. 154(b) by 0 days.

(21) Appl. No.: 16/945,716

(22) Filed: Jul. 31, 2020

(65) Prior Publication Data

US 2022/0036041 A1 Feb. 3, 2022

(51) Int. Cl.
| | |
|---|---|
| *G06V 20/69* | (2022.01) |
| *H04N 5/225* | (2006.01) |
| *G06T 7/00* | (2017.01) |
| *A61B 10/00* | (2006.01) |
| *A61K 35/12* | (2015.01) |
| *G01N 33/569* | (2006.01) |

(52) U.S. Cl.
CPC .......... *G06V 20/693* (2022.01); *G06T 7/0012* (2013.01); *H04N 5/2252* (2013.01); *H04N 5/2256* (2013.01); *A61B 10/0012* (2013.01); *A61K 35/12* (2013.01); *G01N 33/56972* (2013.01); *G06T 2200/24* (2013.01); *G06T 2207/20081* (2013.01); *G06T 2207/20084* (2013.01); *G06T 2207/30024* (2013.01)

(58) Field of Classification Search
CPC . G06V 20/693; G06T 7/0012; G06T 2200/24; G06T 2207/20081; G06T 2207/20084; G06T 2207/30024; H04N 5/2252; H04N 5/2256; A61B 10/0012; A61K 35/12; G01N 33/56972
See application file for complete search history.

(56) References Cited

U.S. PATENT DOCUMENTS

| | | | | |
|---|---|---|---|---|
| 4,099,917 | A  * | 7/1978 | Kim | ................... G01N 33/5094 |
| | | | | 436/17 |
| 4,998,533 | A  * | 3/1991 | Winkelman | ........... A61B 5/411 |
| | | | | 600/479 |
| 2014/0313322 | A1* | 10/2014 | Denise | ................ G01N 33/487 |
| | | | | 348/135 |
| 2021/0333536 | A1* | 10/2021 | Luo | .................... G02B 21/0036 |

FOREIGN PATENT DOCUMENTS

| | | | |
|---|---|---|---|
| JP | 2000309544 A  * | 11/2000 | |
| WO | WO-2018002678 A1 * | 1/2018 | ......... A61B 10/0012 |

* cited by examiner

*Primary Examiner* — Tat C Chio
(74) *Attorney, Agent, or Firm* — Bell Nunnally & Martin LLP (57) ABSTRACT

A system and method of biological testing and deep learning to predict fertility based on ferning patterns and detecting white blood cells in cervical mucous samples.

10 Claims, 9 Drawing Sheets

FERTILITY WINDOW PREDICTION USING A CONVOLUTIONAL NEURAL NETWORK (CNN) AND OTHER LEARNING METHODS

CROSS-REFERENCE TO RELATED APPLICATIONS

This patent application claims priority to U.S. Prov. Pat. App. Ser. No. 62/865,857, filed Jun. 24, 2019, which is hereby incorporated by reference for all purposes.

BACKGROUND

Technical Field

This invention relates to methods, devices, and test kits for use in determining the fertile window progression in female mammals with a focus on humans. More specifically, this invention incorporates biological testing and deep learning algorithms.

Background

One way to track female ovulation is by using a variety of test kits, fertility monitoring devices, or apps. When using any of these techniques, daily observations and physical signs like body temperature, cervical mucus, and urine hormone levels are used to determine the fertile window. Thus, the information obtained from monitoring the phases of fertility and infertility can be used to either achieve or avoid pregnancy. The limitation with any of these methods is they primarily test and capture the biologic signs during the PEAK window (3-5 days) of the female ovulation cycle. In fact, published literature has demonstrated the fertile window can be an 8-9 day progression, which is outside the capabilities, and a limitation, of current fertility monitoring devices.

Figure 8:
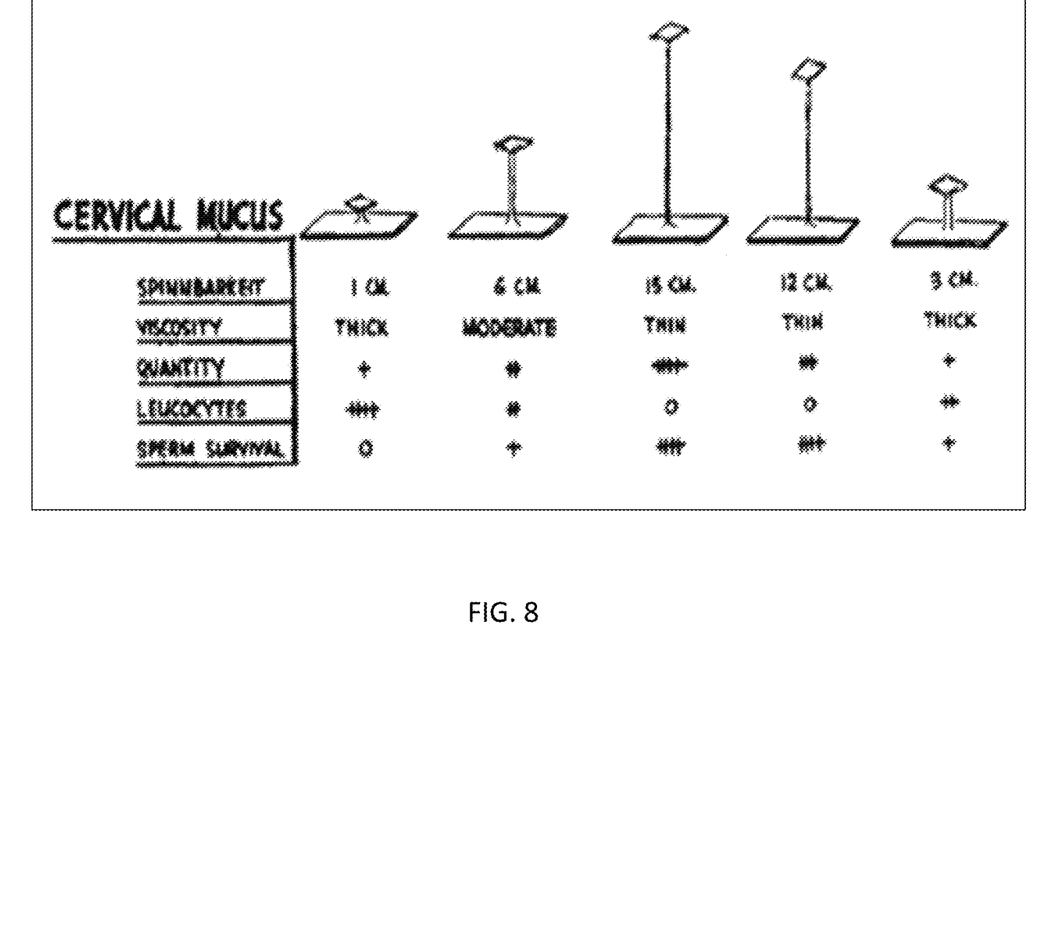
FIG. 8 shows a chart of leukocyte production.
Figure 9:
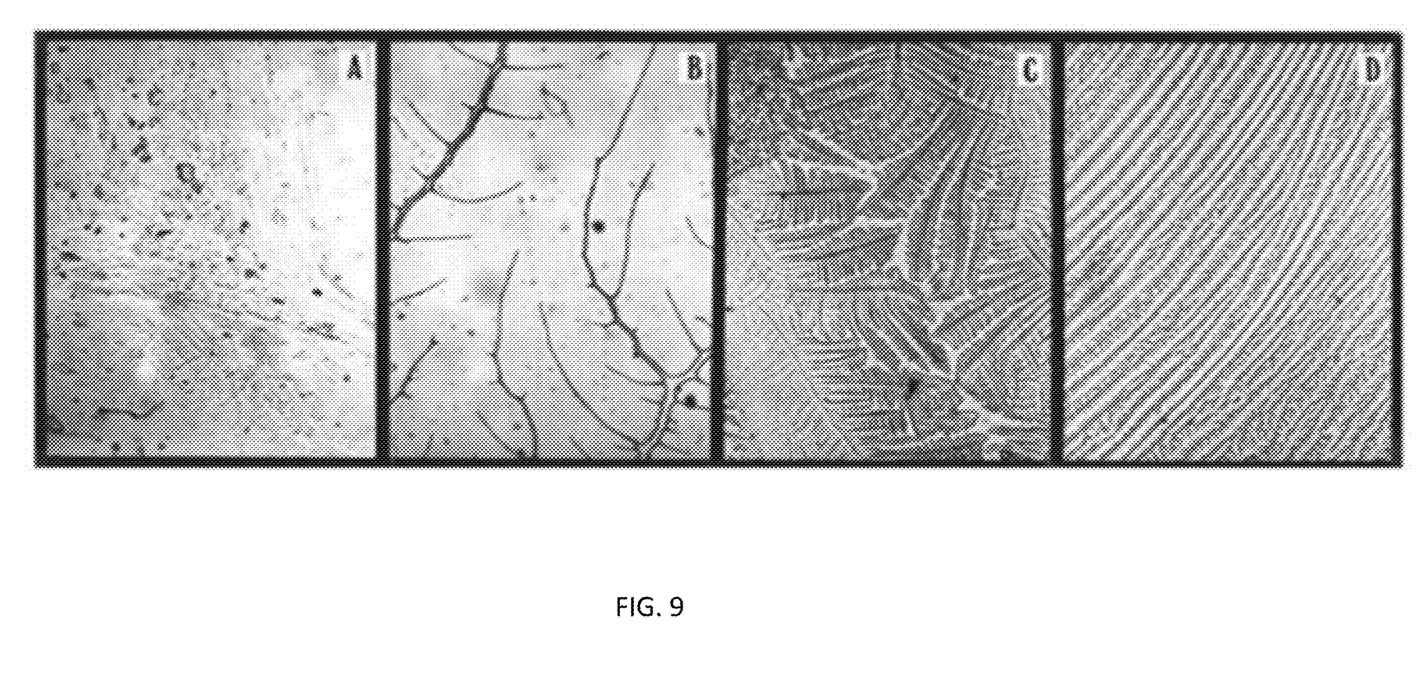
FIG. 9 shows various crystallization ferning patterns.

As the female fertility window approaches, the moment fertility window begins the body reacts in two unique ways. First, the body gradually reduces its leukocyte production to zero within the cervical mucous to create a sperm friendly environment. As shown in FIG. 8 leukocyte production "0" represents the fertility window. Once the fertility window concludes, the leukocyte production dramatically increases to eradicate any remaining residual sperm. Second, as shown in FIG. 9, the crystallization ferning patterns, within the cervical mucous, gradually change (from A to D) leading up to the fertility window (stages C and D). Once the fertility window concludes, the cervical mucous crystallization patterns return to A.

The fertility window is considered the ideal window of time that a woman is most fertile and can conceive. Clinical guidelines have taught the fertility window to be a 4-5 day time period within a 28 day menstrual cycle. Women and couples use a variety of test kits, fertility monitoring devices, or apps that follow the teachings of the 28-day cycle and 4-5 day fertility window. It is now known a woman's own specific physiological cycle can last between 21-56 days, for various reasons. Largely, these monitoring devices do not appreciate the high variability and unpredictable nature of an individual woman's physiological processes in any given cycle.

The conventional teaching of a 28-day menstrual cycle is based on that of healthy women. Broadly, a healthy menstrual cycle steadily increases in estrogen and other hormones rise until it reaches PEAK. PEAK is considered the day of highest estrogen surge within a cycle and is the optimal day for conception/fertilization. Conventional wisdom teaches at day 14 of a 28 cycle (middle of the cycle), the woman experiences ovulation and an egg is released from the ovary. Days before PEAK, the woman's body undergoes physiological, chemical and cellular changes in preparation for incoming sperm and to facilitate a fertilization. The days before and after PEAK are referred to as the fertility window and have conventionally been taught to be a 4-5 day window. As such, various test kits, fertility monitoring devices, and apps monitor the menstrual cycle and fertility window around this 28-day cycle, 4-5 day window teaching.

Fertility apps use the calendar-based method of tracking. This method calculates PEAK and the fertility window based on the assumption and the teaching that women have middle-of-the-month ovulation. Some apps have more sophisticated algorithms which accept additional data for calculations and predictions (e.g., oral temperatures or Luteinizing Hormone (OPK) test results). However, these additional measurements and tests primarily capture the various biologic signs during the PEAK window (4-5 days) of the female ovulation cycle. Clinical studies have demonstrated that 70% of women do not ovulate in the middle of their cycle and can ovulate at different times from month to month and from cycle to cycle, even if the woman's cycle is always the same length. Furthermore, it is estimated that fertility apps have collectively demonstrated a 21% accuracy of fertility window prediction. Simply, fertility apps are limited due to the unpredictability of physiological variations within a woman's menstrual cycle length and ovulation day.

Basal Body Temperature (BBT) is another long-established way of detecting ovulation and fertility window prediction. After ovulation, temperatures rise due the release of progesterone. The BBT method relies on charting multiple temperature measurements, either orally or dermally, throughout a given month to determine ovulation, or PEAK for the upcoming month. However, like fertility apps, BBT methods base predictions on the assumption women experience regular ovulations. BBT methods do not account for the hormonal, cellular, and physiological variabilities for an individual woman in each cycle. Some BBT methods and devices incorporate the tracking of cervical mucous to increase the prediction or accuracy. However, cervical mucous charting is highly variable between any two women. Thus, for 70% of women who experience monthly irregular menstrual cycles deviating from the 28 day, 4-5 day rule, devices that utilize the BBT methods are of little practical use.

Ovulation Predictor Kits (OPK) is another example of ovulation detection. OPKs utilize urine strips to test or monitor Luteinizing Hormone (LH). Because LH peaks up to a day in advance of ovulation, OPKs are helpful in providing a short-term indication of when a woman should try and conceive based on current cycle data. Some OPK's allow multiple tests of LH over a cycle and may combine LH with E3G—a metabolite that allows assessment of the estradiol level—to provide a fertile window prediction. While manufacturers make claims of 99% accuracy, published data demonstrate prediction of ovulation between 70%-84% depending on the publication. Furthermore, OPKs are known to give high rates of false positives for women with ovulatory issues. OPKs are limited in that they can only provide a snapshot at one point in time of the menstrual cycle, and would require a minimum of two tests a day over a 10-20 day range in each cycle to accurately gauge the cycle's current status.

Testing kits, fertility monitoring devices, and apps have limitations because they largely follow conventional teachings (28-day cycle, 4-5 day window) and do not accurately detect the true fertility window for individual women. However, cervical mucous has long been demonstrated to be a very accurate biological marker for true fertility window detection. Beginning in the late 1800's, scientists observed the importance of cervical mucous to human fertility. It was not until the mid-1900's when Dr. John Billings started to recognize the connection between cervical mucous as a marker for ovulation and developed the Billings Ovulation Method in 1966. In 1976, using the Billings Model as a foundation, the Creighton Model Fertility Care System (CrMS) was created and is still widely used today.

In practice, the CrMS model provides women an easy methodology to observe tactile and visual characteristics of the cervical mucous to pinpoint PEAK and the fertility window. Prior to PEAK, the cervical mucous is viscous and visually opaque. As the woman's body surges towards PEAK, the cervical mucous gradually becomes less viscous, clearer, and stretchier. The first day these visual changes begin to occur is considered the first day of the fertility window. At PEAK, the cervical mucous is its least viscous, clearest, and stretchiest. The day following PEAK, there is a significant drop in estrogen whereby the cervical mucous gradually become less clear and stretchy. The day the cervical mucous returns to its viscous and opaque state would be considered the end of the fertility window. The CrMS model has demonstrated the fertility window to be 8-9 days, not 4-5 days. As such, cervical mucous testing devices have been invented in a variety of ways to determine the fertility window.

For example, U.S. Pub. Pat. App. No. 2011/0106465 is an invention to measure the viscosity of cervical mucous. Other devices range from novel ways of sampling, such as in U.S. Pat. No. 4,628,941, to those devices measuring temperature/polarization changes, or water content changes, such as in U.S. Pat. No. 4,151,833, within the mucous. U.S. Pub. Pat. App. No. 2006/0018043, which is incorporated herein by reference, and PCT Pub. App. No. WO/2020/092901, which is incorporated herein by reference, both focus on ferning patterns.

During the follicular phase of the menstrual cycle, the increase of estradiol levels in the blood cause an increase in the salivary electrolytes. This results in a crystallized structure appearance resembling fern leaves. Because hormone levels change throughout the menstrual cycle, the crystallization patterns change and can be used to determine the ovulation period. Ferning patterns within saliva samples can be used to determine ovulation and the fertility window. Image recognition and artificial intelligence can also be used to determine the fertility window.

Over the course of a menstrual cycle, ovulation is characterized by the increased production of estradiol. Referring again to FIG. 9, the increasing estradiol production creates distinct physiological crystallization ferning patterns within the cervical mucous. There is a direct correlation with hormone production and ferning pattern crystallizations. As the female becomes closer to PEAK, the patterns become more linear (Stage D), which facilitate grooves or dendritic channels that sperm can easily travel, whereby the largest number of linear channels are observed during PEAK day itself. Once channels become linear, this day would mark the beginning of the fertility window. In stages A, B, and C, the channels are not linear, whereby sperm cannot easily travel.

White blood cells (leukocytes or WBC) are the body's defense against pathogen invaders. The female body considers sperm a pathogen invader. Over the course of the menstrual cycle, the WBC counts within cervical mucous gradually decrease. Once the fertility window begins, the WBC presence within cervical mucous plummets, allowing sperm to stay and not be removed by the female's immune system. Once the fertility window closes, the WBC production increases, clearing out any pathogen invaders, including unfertilized sperm.

Ferning channels and WBC absence presents a unique biological identifier that teaches away from conventional monitoring methods relying on normal hormone fluctuations. Assuming women experience normal menstrual cycles, then hormones will gradually increase, causing proportional physiological changes to the body (e.g., temperature). PCT Pub. App. No. WO2020/092901 discloses a device for imaging ferning patterns within saliva to determine ovulation, however this device has limitations. Although it images ferning patterns, saliva ferning patterns are subject to hormone fluctuations like other conventional markers and teachings. In other words, ferning patterns from saliva does not provide unique characteristics, biological markers, or accuracy detection for the 70% of women who experience irregular menstrual cycle due to hormone fluctuations.

In 1972, the World Health Organization likened the uterine cervix to that of a "biological valve. In this context, when the female body is fertile, the cervix creates a biologic window of opportunity regardless of fluctuating hormones or irregular cycles. The cervix biology changes at the cellular level, not the hormone level, to increase the chances for fertilization. First, the cervix eliminates the presence of white blood cells. White blood cells are the body's immune cells responsible for removing pathogen invaders and foreign bodies and male sperm would be considered a foreign body to the female. Secondly, the cervical mucous creates linear channels for the sperm to move quickly. Analogous to lanes or highways, the cervical mucous orients these linear channels directly towards to incoming egg at widths specifically designed for sperm, and a viscosity that makes swimming faster. Once the fertility window closes, the biological valve closes. The channels are immediately turned horizontal to act like walls preventing forward movement. Furthermore, the cervical mucous allows the presence of WBCs again to remove foreign invaders. Regardless of hormones, these distinct cellular characteristics can only be observed within the cervical mucous.

White blood cell counts and imaging can also correlate with other biological markers as a methodology of determining the current phase of the ovulation cycle. For example, progesterone during ovulation has been shown to correlate positively with white blood cell and neutrophil counts. Because of increased estrogen levels, neutrophil release is promoted within bone marrows to defend against infection during the fertilization process. Therefore, quantification of WBCs/neutrophils can give further insight to females beyond fertility, such as hormone deficiencies, conditions related to hormones (e.g., Poly Cystic Ovarian Syndrome), or women who are postpartum.

Women that collect and assess their fertility with their own physiological data (basal body temperature, cervical mucous, etc.) have a huge burden determining whether they are ovulating. First, this data must be recorded daily and analyzed for accurate prediction. Furthermore, these biomarkers can only detect the ovulation period within a window of 3-5 days. While the CrMS method improves the fertility range accuracy to 8-9 days, its data collection is also subjective data by the woman. This is particularly burden-some for women who have underlying hormone conditions that fluctuate or even healthy women who are postpartum. Women who are breast feeding or postpartum have also been studied extensively with hormonal correlation. Hormones greatly fluctuate for these women as their body provides for an offspring and may cause unpredictable mucous characteristics. For these women, in may be difficult to accurately determine fertility. Thus, there is need for an objective device and methodology for correlating WBCs and ferning patterns to hormone levels.

SUMMARY OF THE INVENTION

To observe fertility-related changes (decreased leukocytes, increased ferning crystallizations within cervical mucous and/or saliva, and other changes), the present invention consists of a visual learning algorithm with a test kit comprising one or more of the following features: swabs to test leukocytes, swabs to examine ferning patterns in cervical mucus, and swabs to examine ferning patterns in saliva. In various embodiments, the visual learning algorithm utilizes a convolutional neural network (CNN) or other learning algorithm associated with machine learning or deep learning applications. Ultimately, in addition to predicting the most fertile time period within the fertile window, this visual learning algorithm may predict the true starting and ending date of the fertile window with superior accuracy and confidence compared to similar technologies.

In various embodiments, devices, systems, and methods are provided for imaging ferning patterns and WBC presence within cervical mucous. In one embodiment, the device correlates ferning patterns and WBC presence to help users monitor their individual menstrual cycle and objectively detect their individual fertility window. Additionally, computer learning models and vision models may be incorporated to learn various other relationships between ferning patterns and WBC presence. For example, statistical analysis can correlate ratios to biological conditions and/or health behaviors related to fertility. Various embodiments may provide a relatively low-cost automated solution for individualizing fertility monitoring and cycle monitoring based on biological characteristics of the cervical mucous.

Various embodiments describe a system that images biological characteristics of cervical mucous corresponding to various relationships between the menstrual cycle and fertility window. The device relies on data from ferning patterns and WBCs within cervical mucous. The system may include an optical assembly capable of moving in multiple axes with an optical camera and one or more objective lenses. The camera and optical assembly are aligned to visualize a sample specimen contained within a slide chamber or cartridge. The system may utilize an array of LED lights, in various patterns, underneath a motorized tray to illuminate the sample specimens from various angles. Furthermore, the system may utilize a ratio of saline, as an analyte, to darken aspects of the sample specimen to increase the accuracy and prediction when processed in a CNN vision model.

In accordance with another aspect, WBCs and stages of ferning are correlated to one another to determine the beginning and end of the fertility window. For an individual, the absence of WBCs is correlated to the ferning patterns to mark the beginning of the fertility window. For the individual, the first presence of WBCs marks the end of the fertility window. Images are captured and stored to learn the variable ferning patterns to WBC presence. A CNN may be used to determine patterns and correlations from a large database of images to determine the various stages of the menstrual cycle, including the beginning and end of the fertility window.

In accordance with another aspect, the device may determine methods of correlations and ratios to determine the stage of the menstrual cycle, disease conditions, or factors that cause fluctuations of hormone levels. For example, female hormone levels are largely associated with characteristics of health behaviors (obesity, stress, smoking, etc.). This method and ratio recognition may include data inputs from an individual about various characteristics related to health and living. This method could also include the hormone analysis and current disease state of the individual. The device may utilize computer learning models to analyze data and images to determine variables or analytes of statistical importance, i.e., referring to the importance or influence a metric has making an accurate learning model prediction in relation to image analysis. Statistical analysis may be used to find ratios and patterns indicative of a biological condition or disease of the individual and may be used to increase accuracy with respect to other individuals. This may be particularly beneficial for individuals who are unaware of hormone conditions, potentially undiagnosed diseases related to hormones, or health behaviors that are contributing factors.

The above summary of the invention is not intended to represent each embodiment or every aspect of the present invention. Embodiments may include one, some, or none of the listed advantages.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION

The present invention is directed towards systems and methods for biological testing and deep learning that can be used to predict fertility windows.

In one aspect, these characteristics can be used to determine the personalized fertility window by objectively correlating WBCs to ferning patterns. For example, image recognition models and computer models, such as a convolutional neural network, may be used to correlate the absence of WBCs to ferning patterns; the presence of WBC to ferning patterns, and linear ferning patterns to WBCs. These three points mark the beginning, PEAK, and end of the fertility window. In one aspect, a device may be used to detect the presence or absence of WBC and ferning linearity.

Furthermore, the device may be used to collect various points around these three points and compare images and statistics against stored data. Therefore, the device may provide users with a tool to progressively monitor and gauge multiple points along an individual fertility window. This device may be beneficial to many individuals, including women with menstrual cycle irregularities and/or women who have difficulty in objectively determining the fertility window for the purposes of achieving or avoiding pregnancy.

In another aspect, a device is provided that can determine various points along the menstrual cycle. Throughout the menstrual cycle, hormones increase in preparation for ovulation. Furthermore, WBC proportionally decrease along with ferning pattern changes. Correlations of WBC to ferning pattern characteristics can be used to plot various points along the menstrual cycle. A user can sample cervical mucous to gauge where the user is within a menstrual cycle.

In another aspect, a device is provided that can determine a biological condition from ferning patterns and WBCs within the cervical mucous and various health inputs. For example, polycystic ovary syndrome (PCOS) is the most common cause of anovulatory infertility. PCOS is a hormone condition largely caused by an accumulation of health behaviors, but true underlying causation is uncertain. In various embodiments, the device may allow for descriptive health variable inputs (i.e., known disease conditions, health behaviors, obesity, stress, smoking, drinking, medications, etc.). In this example, ferning patterns, WBCs, and health behavior data associated with PCOS can be compared and analyzed against stored data. Computer models and image recognition can be utilized to determine variables of importance in subjects with PCOS against those without PCOS. This aspect can be helpful information to subjects with infertility problems who are progressing towards PCOS or unaware they have PCOS so they can proactively seek medical intervention.

In another aspect, image recognition can be utilized to correlate ferning pattern characteristics to a biological condition. For example, PEAK is considered the time point when ferning patterns are most linear. Image recognition can be utilized to measure the spacing between linear channels during PEAK and uncover an ideal width for achieving pregnancy at PEAK. Computer models and statistical analysis can be utilized to determine health behavior variable(s) of importance (i.e., smoking) that cause linear spacing to reduce. This is an example of a correlation that has never been proposed or analyzed.

Figure 1:
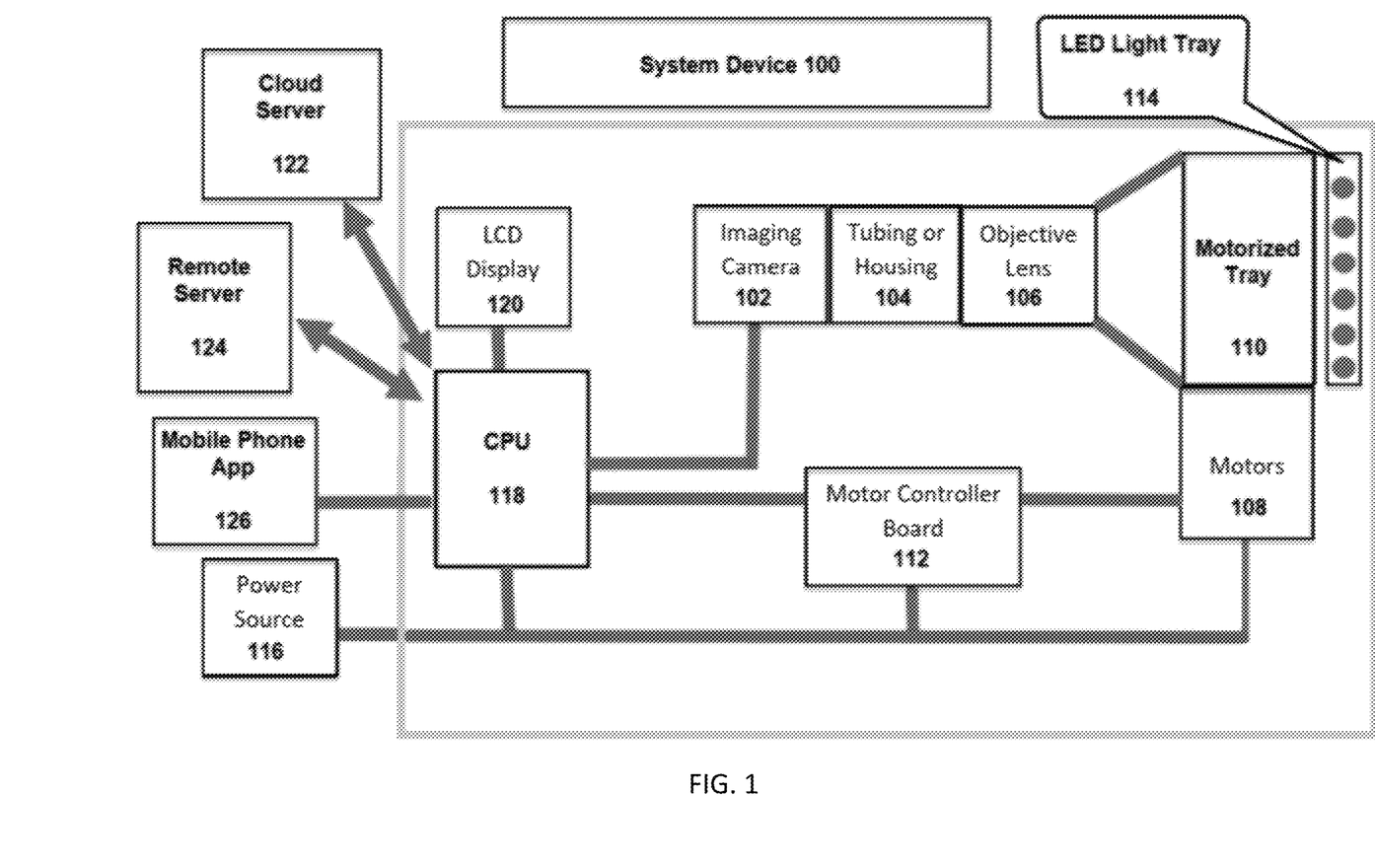
FIG. 1 shows a diagram of a system according to an embodiment.

Referring now to FIG. 1, the system 100 includes an optical camera assembly comprising: an imaging camera 102, tubing or housing lenses 104, and a magnified objective lens 106. In one embodiment, the imaging camera 102 is attached to the lens housing or tubing, whereby the lens tubing 104 or housing is attached to a magnified objective lens 106. The length of the lens housing 104 is dependent on the resolution of the imaging camera 102 and magnified objective lens 106 being used. For example, a 20-megapixel camera using a 10× magnification requires a lens housing length of 8.5 inches for optimization, whereas a 5-megapixel camera at 100× magnification requires a shorter housing. The camera, housing, and objective lens could be arranged in a variety of ways depending on the computer vision model and fine tuning for accuracy. Various embodiment may utilize a camera assembly to produce black and white images and/or color image for processing. The camera assembly may be powered by motors 108 and controlled by a microprocessor 112 to move in the X, Z axis. In some embodiments, the camera assembly can be programmed to adjust its height in the Z axis based on focusing needs and calibration adjustments.

Figure 2:
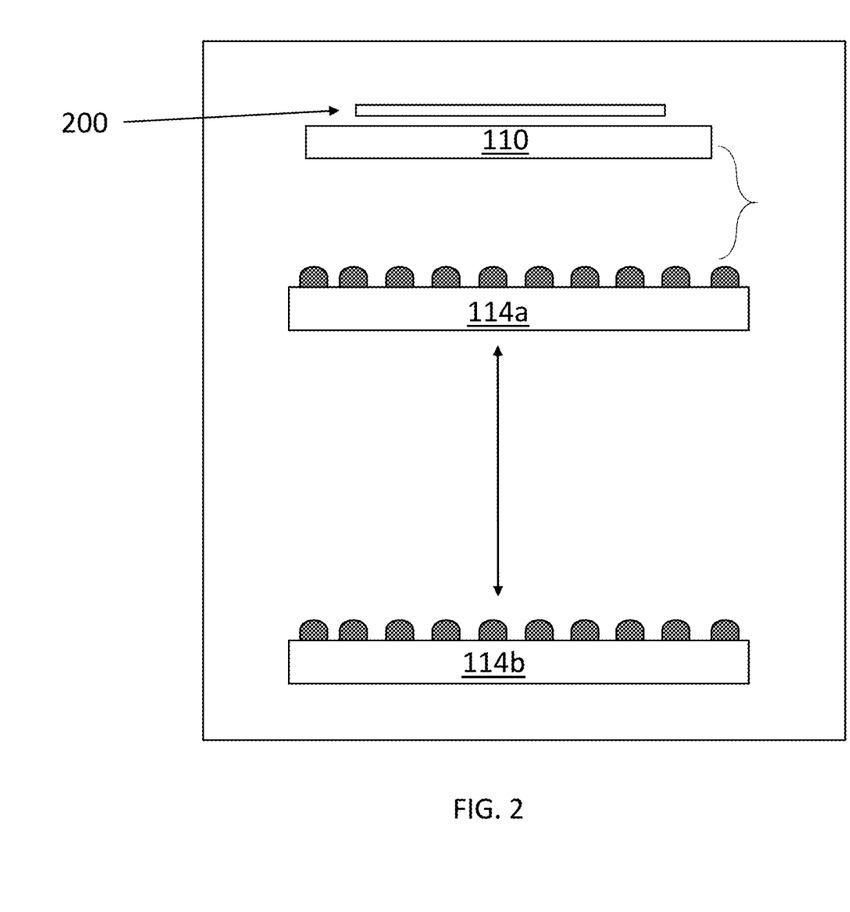
FIG. 2 shows a movable LED array according to an embodiment.

In another aspect, the system 100 includes an LED light source assembly for visualization. Referring now to FIG. 2, the LED lighting 114 may be positioned in a distance between, for example, 5 mm (shown as 114a) and 200 mm (shown as 114b) from the motorized sample tray 110 holding slide 200. The distance may be adjusted by a user and/or the camera's imaging software. For example, a closer LED distance to the sample tray 110 would give more lighting, which may require less gain and exposure adjustments within the camera imaging software. A further distance of the LED light would be the opposite. In some embodiments, the LED can be positioned in a tray 114 connected to the motorized sample tray 110. The LED may illuminate the specimen sample at a minimum of 5 mm offset from camera assembly's Z axis. For example, if the camera assembly is in a fixed (0,0) X, Y position, then the LED light will be fixed 5 mm offset from the (0,0) position and below the sample specimen somewhere between 5 mm and 200 mm.

In other embodiments, the LED light pattern array 114 adjusts with the camera movements. Some embodiments may rely on a randomized method of counting and move the camera assembly to a random X,Y coordinate. For example, a sample specimen is placed on the motorized tray 110. Next, the camera calibrates and detects the sample slide and its borders. Next, the computer program randomly selects an X, Y coordinate to visualize the slide specimen and moves the camera assembly. For a given (X, Y) coordinate, the microprocessor 112 illuminates an LED light or light pattern 114 that is a minimum 5 mm offset from the camera assembly's Z axis. In this manner, the LED light or lights avoid direct illumination that is in-line with the camera assembly's Z axis, such as the embodiment shown in FIG. 6B. Furthermore, the offset may create aspects of the imaging technique used for computer vision models.

In various embodiments, multiple LED lights can be fixated inside an LED tray 114 somewhere between 5 mm and 200 mm below the sample specimen. An LED light tray 114 may be attached to the motorized stage 110 controlled by motors 108 to move in the Y axis.

The offset of LED illumination creates shadow features to the sample specimen. Various embodiments utilize a method of saline, described below, to create distinct contrasts and borders within the sample specimen. The offset of LED lighting further accentuates these contrast features and borders of the specimen 2D images. Collectively, this method optimizes image inputs to the CNN 300 to distinguish pixels, borders, shapes, and clarity for higher accuracy and prediction.

Figure 3A:
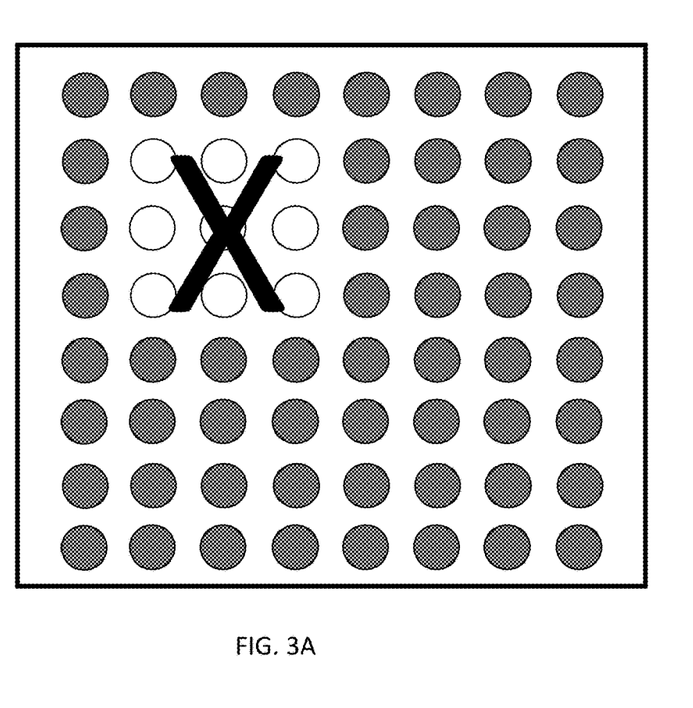
FIGS. 3A and 3B show an LED array according to an embodiment.
Figure 3B:
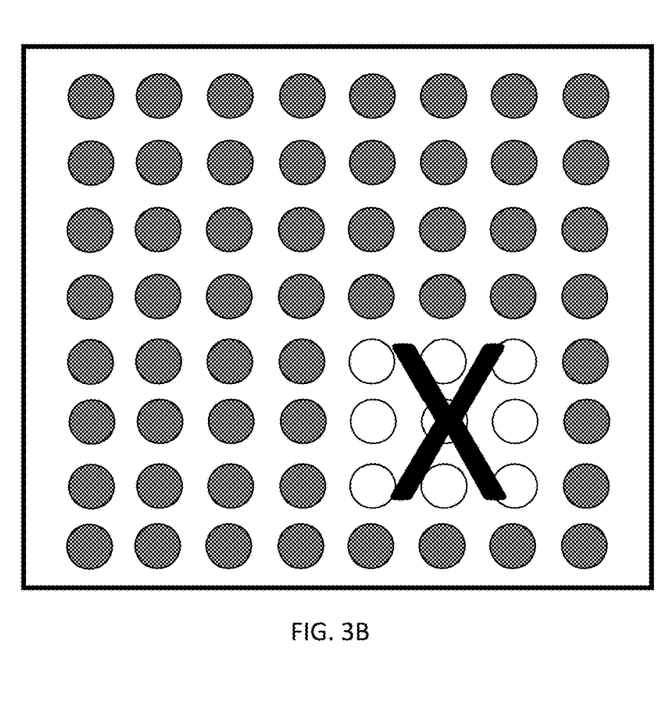
Figure 6A:
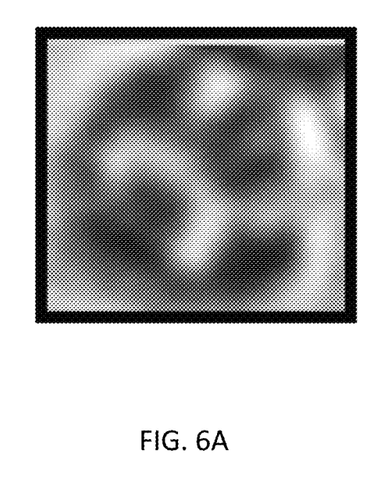
FIGS. 6A and 6B show an image of a white blood cell and an imaging device according to an embodiment.
Figure 6B:
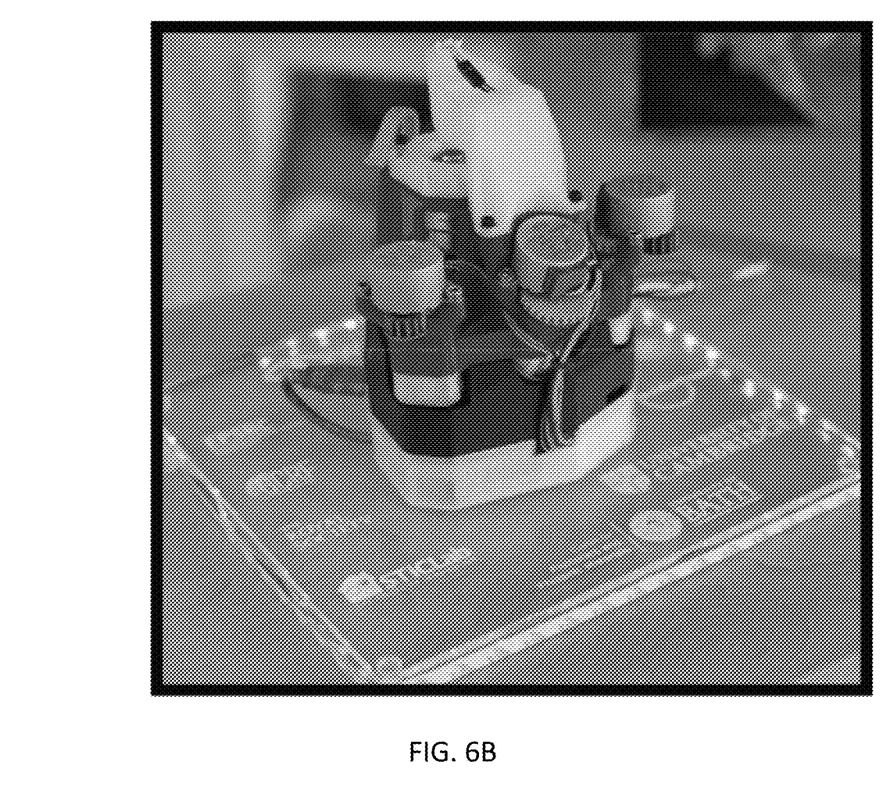

Referring now to FIGS. 3A and 3B, a method is provided to visualize cells ranging between 2-30 microns in size, and their individual characteristics at 2D. In other embodiments, a 3D composite image can be created from consecutive 2D images. In one embodiment, the camera assembly first goes to a random X, Y coordinate and is fixated. Next, the microprocessor illuminates an LED pattern below the sample specimen. Images and LEDs are synchronized and activated to capture consecutive images. The individual images create shadows and depths of the sample specimen, both internally and externally, at the various angles. Furthermore, because various parts of a cell structure have different permeabilities, the saline analyte technique, described herein, creates contrast and darkening to various aspects, or shadows, to parts of a cell—both internally and externally. FIG. 6A shows a depiction of a WBC at one angle using this technique. Consecutive 2D images are sent for processing to create a 3D composite using computer vision models. One example of a 3D reconstruction computer vision model is volume carving, which is a well-known shape-from-silhouette reconstruction technique.

Figure 4A:
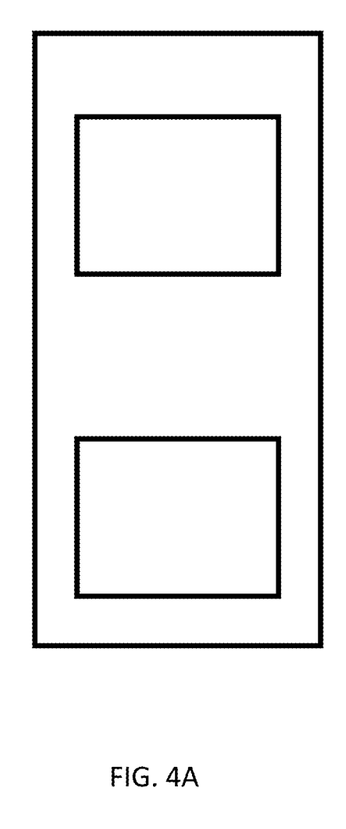
FIGS. 4A and 4B show a slide according to an embodiment.
Figure 4B:
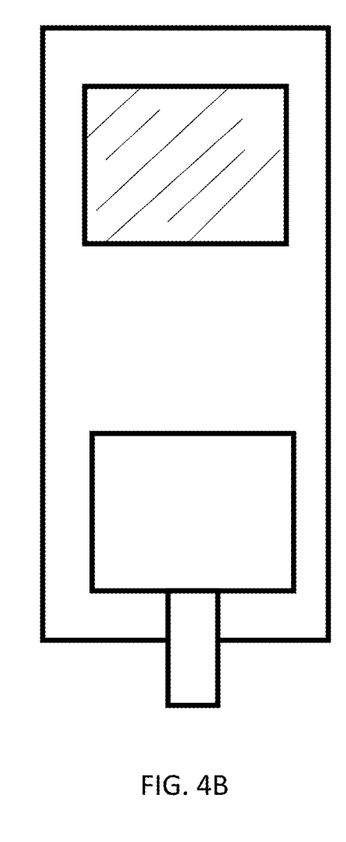

In another aspect shown in FIG. 2, the system includes the use of a slide or slide cartridge 200 containing the specimen sample. In one embodiment, the slide 200 could contain one or multiple chambers for sampling. For example, as shown in FIG. 4A, the Leja 20-micron, 2 chamber glass slide could be included as a disposable item for the end user. As shown in FIG. 4B, a 20-micron sample of cervical mucous would go in one chamber and allowed to dry. In the other chamber, a 20-micron sample of cervical mucous is mixed with saline.

In another embodiment, the slide cartridge can be a plastic disposable integrated with accurate sampling pipettes and preloaded with saline, wherein one chamber can be for dry mucous sampling and the other pre-loaded with the saline. The device could also contain magnetic feet for reproducible placement on the motorized tray 110. Such a cartridge may be useful for everyday consumers who have little training in sampling techniques.

In another aspect, the system executes a counting method based on randomization, for example, using a camera assembly capable of moving in the X axis and a motorized tray 110 that moves in the Y axis. First, the microprocessor adjusts the camera up and down (Z axis) for calibration and identification of the slide cartridge borders to confirm its home position (0,0). Next, the computer program generates a plurality of predetermined or random X, Y coordinates from the (0,0) position to capture images. The end user could specify the number of X, Y coordinates, whereby higher the randomizations, the higher the accuracy of cell counting.

In another aspect, a novel use of saline as an analyte for WBC imaging is provided. U.S. Pat. No. 4,099,917, which is incorporated herein by reference, describes a similar method, however the current method is distinct in several ways. For one, the current method does not utilize any detergents or anticoagulants like the referenced prior art. Two, the prior art method relies on imaging techniques of light scatter whereas the current method does not. Third, the prior art method requires incubation times, whereas the current method with the current device is ready to use not requiring any incubation times. Fourth, the current method does not require high powered magnification and imaging techniques. Last, although other ratios can be used, the current method is optimized when the sample is on the order of a range of 1:50 to 1:100 ratio of sample to saline. For example, in one embodiment, a 1 microliter sample of mucous may be mixed with 50 to 100 microliters of saline solution. In some embodiments, the saline solution has a concentration of 0.9% salt in distilled water. Below this, the ratio does not darken or accentuate sample features as well and ratios beyond this may cause cell destruction. Around this ratio, contrast is provided as well as swelling. The swelling aspect helps 3D composite image techniques and accentuates features of a specimen. Furthermore, the saline sampling method allows easier detection and identification within various computer vision models for accuracy and prediction.

Another aspect describes identification of individual biological cells, and their characteristics, using saline and computer vision models. For example, cervical mucous may contain WBCs. Monocytes and neutrophils are two examples exhibiting visually different, and distinct characteristics. Under normal circumstances, high powered, expensive magnification equipment is needed to distinguish between the various subtypes of WBCs. However, saline creates contrasting and darkened effects inside and outside of cells that can be imaged using LED lights at various angles and patterns with the current device. In some embodiments, the LEDs may have a wavelength on the order of between 400-700 nm. These images are processed using various computer imaging models (blob detection, edge detection, pixel densities, composite imaging, volume carving) to distinguish, discriminate, and quantify the individual cells.

In other embodiments, this saline technique can also be used to image white blood cells, red blood cells, and platelets from blood. For example, cervical mucous samples can sometimes be accompanied by residual blood during the menstrual cycle. The current saline technique may accurately identify and quantify RBC and platelets from WBCs.

Another aspect describes imaging ferning patterns of a dried sample of cervical mucous. The cervical mucous can be manually obtained or with various collection devices. For example, a microfluidic device can be fashioned to separate WBCs within cervical mucous into one chamber and the viscous cervical mucous into another chamber or the cervical mucous can be placed on various slides at various depths and heights. Regardless of the collection method or device, the cervical mucous is allowed time to dry for ferning patterns and crystallizations to form. The current device allows the end user to adjust the baseline Z-axis of the camera imager depending on the collection device. For example, end users may use different commercial slides of various heights requiring baseline focus adjustments. Aspects of this device allow the end user to adjust the Z-axis and store details for future imaging.

Another aspect describes image data that is processed by a convolutional neural network computer vision model, such as is described in PCT Pub. App. No. WO2017/146813, which is incorporated herein by reference. It is understood that a CNN regressively works through its convolutional layers and operations to extract patterns and features of input images. Images are passed through each convolutional layer with its associated filter. Following each convolutional layer, a Rectified Linear Unit is applied, and information is pooled. This process continues until its output is classified.

CNN may be used for image analysis. Mechanics of a CNN vision model include image capturing, pattern recognition, data training, various models of a CNN, classifiers, and general assemblies. The illustrated CNN's first convolutional layer applies a standard 3×3 convolution, with a plurality of additional convolutional layers that apply depth-wise convolutions. In one example, the CNN can include thirteen convolutional layers, each comprising a depth-wise convolution, followed by a pointwise convolution. Each convolutional layer is followed by a rectified linear unit (ReLU) and batch normalization. The last layer is an average pooling layer that reduces the spatial resolution to one followed by a fully connected layer that is fed to a classification layer for detection. Down sampling may be addressed with strided convolution in the depth-wise convolutions as well as in the first layer. The classification layer may be added at the end and trained to classify the cervical mucous ferning samples into classifications, such as A, B, C, and D shown in FIG. 9.

The training data includes multiple training examples, with each training example including one or more images of WBC, ferning patterns, and/or statistics about these respective images. Additionally, training data can correspond to various inputs of health variables. It is understood the system 100 trains the CNN 300 and statistical computer 302 networks on the training data. For example, as the CNN processes pixel inputs of each black and white image, an error between the pixel values is generated by the CNN 300 and the pixel values in the corresponding black and white image in the training data.

Figure 5:
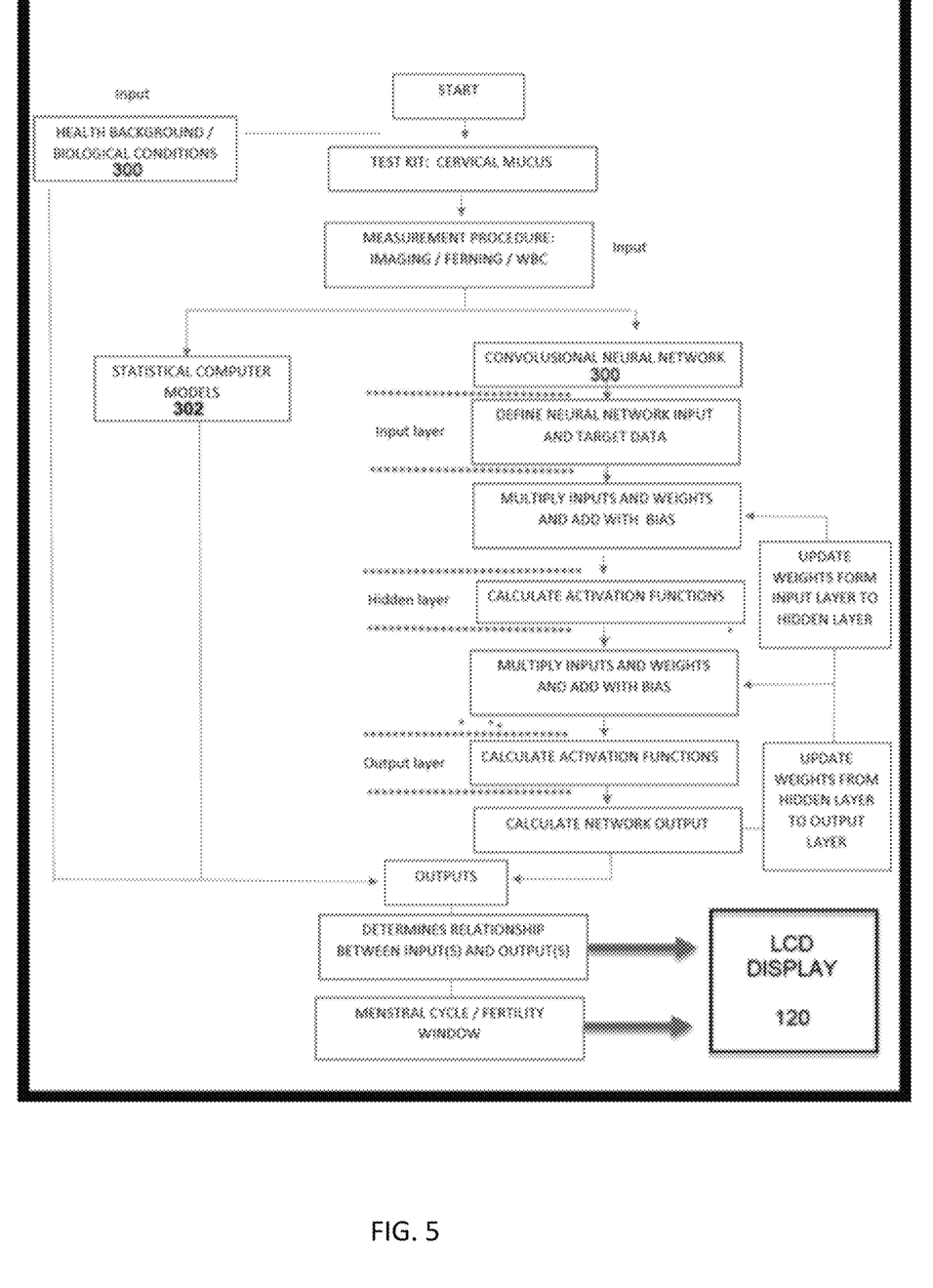
FIG. 5 shows a flowchart according to an embodiment.

FIG. 5 shows a flow diagram of the system in practice, whereby the CNN 300 process is described. The system uses the weights to update values of the parameters used in each layer of the CNN 300 training techniques, e.g., stochastic gradient descent with backpropagation.

The system trains the CNN 300 on the training data. That is, the system processes each training image using the CNN 300 to determine a predicted feature vector for the training image. The system then determines an error between the predicted feature vector for the training image and the feature vector corresponding to the training image in the training data and uses the error to update values of the parameters used in each layer of the cell characteristic neural network using conventional neural network training techniques.

For a system of one or more computers to be configured to perform particular operations or actions, the system has installed on it software, firmware, hardware, or a combination of them that, in operation, cause the system to perform the operations or actions. For one or more computer programs to be configured to perform particular operations or actions, the one or more programs include instructions that, when executed by data processing apparatus, cause the apparatus to perform the operations or actions.

In another embodiment, the statistical computer model 302 is understood to be machine learning models and statistical calculations, i.e., two different learning models may be utilized in conjunction to first identify images and then make predictions.

In practice, image data is processed within the CNN 300 and statistical/variable data is processed in the statistical computer model 302. For example, the system device 100 prompts the user for health data inputs (e.g., biological conditions, underlying causations, or other health variables) before WBCs and ferning patterns are imaged. The CNN 300 vision models are understood to be images, statistical measurements, patterns, and quantifying WBC and ferning images, respectively. Simultaneously, health data inputs may be sent.

It is understood these machine learning models can be supervised, unsupervised, or reinforcement machine learning models depending on the variables. The inputs from the system are provided to a CNN 300 and machine learning network 302 to determine variable points along the menstrual cycle and definition of the fertility window. Preprocessed images are used for comparison and training in the CNN 300, and stored training variables are used within the machine learning network 302.

In other embodiments, the system and its computer learning models 300, 302 can be implemented on a cloud computing system 122, a remote server 124 that is accessed by the system 100 via a network connection, or stored locally on the system's memory, e.g., mobile phone, device or the system's microprocessor. In yet another aspect, the current device contains a graphical user interface (GUI) 120 configured to display statistical results or imaging results from the CNN 300 or statistical computer database 302. For example, the GUI can display the absence of WBCs and linear ferning patterns, indicating the user is at PEAK. In another aspect, these results can be configured to connect through an app over a phone or other device 126.

Figure 7:
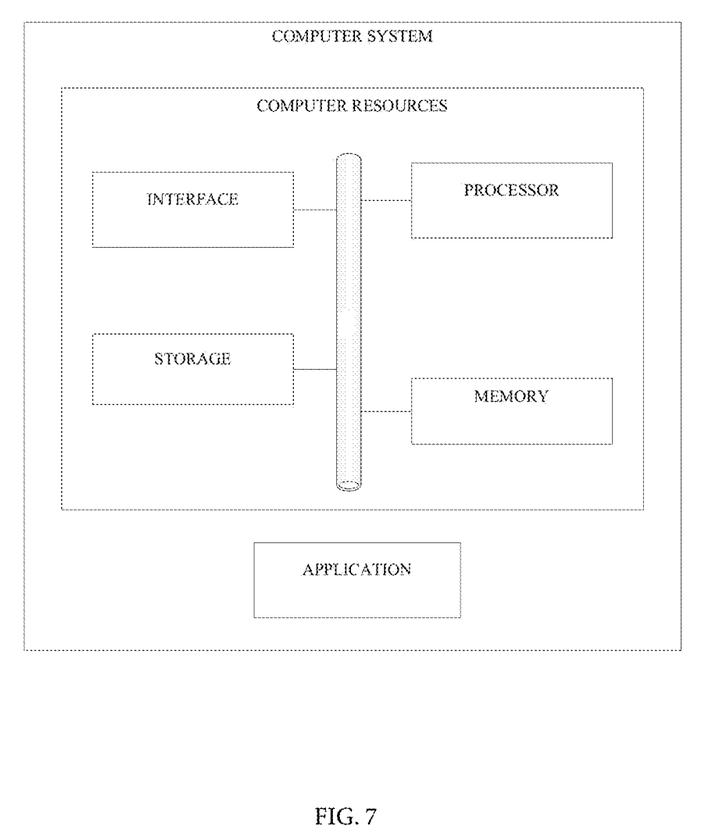
FIG. 7 shows a diagram of a system according to an embodiment.

FIG. 7 is a schematic block diagram illustrating an exemplary system of hardware components capable of implementing examples of the systems and methods disclosed in FIG. 5. The system can include various systems and subsystems. The system can be a personal computer, a laptop computer, a workstation, a computer system, an appliance, an application-specific integrated circuit (ASIC), a server, a server blade center, a server farm, etc.

In operation, the system can be used to implement one or more parts of a system for automatically determining a biological condition of a subject from ferning patterns. Computer executable logic for implementing the system resides on one or more of the system memory, and the memory devices in accordance with certain examples. The processing unit executes one or more computer executable instructions originating from the system memory and the memory devices. The term "computer readable medium" as used herein refers to a medium that participates in providing instructions to the processing unit for execution and can include multiple discrete physical units.

The system can includes a system bus, a processing unit, a system memory, memory devices, a communication interface (e.g., a network interface), a communication link, a display (e.g., a video screen), and an input device (e.g., a keyboard and/or a mouse). The system bus can be in communication with the processing unit and the system memory. The additional memory devices, such as a hard disk drive, server, stand-alone database, or other non-volatile memory, can also be in communication with the system bus. The system bus interconnects the processing unit, the memory devices, the communication interface, the display, and the input device. In some examples, the system bus also interconnects an additional port (not shown), such as a universal serial bus (USB) port.

The processing unit can be a computing device and can include an application-specific integrated circuit (ASIC). The processing unit executes a set of instructions to implement the operations of examples disclosed herein. The processing unit can include a processing core.

The additional memory devices can store data, programs, instructions, database queries in text or compiled form, and any other information that can be needed to operate a computer. The memories can be implemented as computer-readable media (integrated or removable) such as a memory card, disk drive, compact disk (CD), or server accessible over a network. In certain examples, the memories can comprise text, images, video, and/or audio, portions of which can be available in formats comprehensible to human beings. Additionally or alternatively, the system can access an external data source or query source through the communication interface, which can communicate with the system bus and the communication link.

In various embodiments, improvements to this current testing methodology could include data inputs from other types of physiological or biological data. Basal body temperature, urine analysis, hormone analysis, or saliva analysis could be additional inputs. In some embodiments, the device may allow the end user to add customization of variable inputs within the software. For example, an end user may want to include urine analysis as an additional variable to the WBC/ferning pattern correlation.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications, and substitutions without departing from the spirit and scope of the invention. What have been described above are examples of various embodiments of the present invention. It is, of course, not possible to describe every conceivable combination of components or methodologies, but one of ordinary skill in the art will recognize that many further combinations and permutations are possible. Accordingly, the present invention is intended to embrace all such alterations, modifications, and variations that fall within the scope of the appended claims.

What is claimed is:

1. A method to predict a fertility window of a mammal, the method comprising:
providing a housing having a slide holder, a light source, and a camera;
providing a slide having first and second reservoirs;
placing a first mucous sample in the first reservoir and a second mucous sample in the second reservoir;
wherein the first mucous sample is a cervical mucous of a subject mixed with a saline solution at a ratio of at least 1:50;
inserting the slide into the slide holder;
capturing one or more images of the first mucous sample and the second mucous sample; and
analyzing the one or more images to determine whether white blood cells are present within the first mucous sample and identify ferning patterns within the second mucous sample.

2. The method of claim 1, wherein the saline solution has a concentration on the order of 0.9% salt.

3. The method of claim 1 and further comprising:
drying the second mucous sample on the slide, wherein the second mucous sample is a cervical mucous of a subject;
providing the one or more images to a computer vision model; and
determining, at the computer vision model, if the one or more images contain a ferning pattern indicative of a biological condition of the subject.

4. The method of claim 1, and further comprising analyzing the one or more images to determine whether red blood cells are present within the first mucous sample.

5. The method of claim 1, wherein the saline solution does not contain a detergent or anticoagulant.

6. A system comprising:
a housing comprising a camera having a field of view, a light source configured to provide illumination to the field of view, and a slide holder configured to hold a slide containing a cervical mucous sample from a subject such that at least a portion of the slide is disposed within the field of view; and
a computer system comprising one or more processors programmed to execute computer program instructions that, when executed, cause the computer system to:
capture, using the camera, a first image of the cervical mucous sample;
move the light source relative to the slide;
capture, using the camera, a second image of the cervical mucous sample; and
analyze the first image and the second image using a visual learning algorithm to determine if there are white blood cells in the cervical mucous sample; and
wherein the computer program instructions are configured to estimate a fertility window of the subject based at least in part on the determination by the visual learning algorithm that there are no white blood cells in the cervical mucous sample.

7. The system of claim 6, wherein the computer program instructions are configured to identify any ferning patterns in the cervical mucous sample.

8. The system of claim 7, wherein the computer program instructions are configured to correlate a biological condition of the subject to characteristics of the ferning patterns identified in the cervical mucous sample.

9. A system comprising:
a housing comprising a camera having a field of view, a light source configured to provide illumination to the field of view, and a slide holder configured to hold a slide containing a cervical mucous sample from a subject such that at least a portion of the slide is disposed within the field of view; and
a computer system comprising one or more processors programmed to execute computer program instructions that, when executed, cause the computer system to:
capture, using the camera, a first image of the cervical mucous sample;
move the light source relative to the slide;
capture, using the camera, a second image of the cervical mucous sample;
analyze the first image and the second image using a visual learning algorithm to determine if there are white blood cells in the cervical mucous sample;
wherein the computer program instructions are configured to identify any ferning patterns in the cervical mucous sample; and
wherein the computer program instructions are configured to determine a biological condition of the subject based on the determination there are white blood cells in the cervical mucous sample and the ferning patterns identified in the cervical mucous sample.

10. The system of claim 9, wherein the biological condition is fertility disorder caused by PCOS.

* * * * *